United States Patent [19]

Sarantakis

[11] 4,253,997

[45] Mar. 3, 1981

[54] ANTI-OVULATORY DECAPEPTIDES

[75] Inventor: Dimitrios Sarantakis, West Chester, Pa.

[73] Assignee: American Home Products Corporation, New York, N.Y.

[21] Appl. No.: 104,599

[22] Filed: Dec. 17, 1979

[51] Int. Cl.$^3$ .................... C08L 37/00; C07C 103/52
[52] U.S. Cl. ............................ 260/8; 260/112.5 LH
[58] Field of Search .......................... 260/112.5 LH, 8

[56] References Cited

PUBLICATIONS

Matsuo, et al., Biochem. and Biophys. Res. Commun., 43, (1971), 1334–1339.
Rees, et al., J. of Med. Chem., (1974), vol. 17, 1016–1019.
Beattie, et al., J. of Med. Chem., 18, (1975), 1247–1250.
Rinier, et al., Life Sciences, 23, (1978), 869–876.
Yabe, et al., Chem. Pharm. Bull., 21, (1976), 3149–3157.

*Primary Examiner*—Delbert R. Phillips
*Attorney, Agent, or Firm*—Richard K. Jackson

[57] ABSTRACT

The compounds D-p-Glu-D-Phe-D-Nal(1)-L-Ser-L-Tyr-X-L-Leu-L-Arg-L-Pro-Gly-NH$_2$ where X is D-Nal(1), D-Trp, D-Phe, D-Tyr, D-Lys, D-Met, D-Ala or D-Pgl and pharmaceutically acceptable salts thereof exhibit antiovulatory activity in female mammals and are useful contraceptive agents.

11 Claims, No Drawings

ANTI-OVULATORY DECAPEPTIDES

BACKGROUND OF THE INVENTION

The amino acid sequence of leuteinizing hormone releasing hormone (LH-RH) has been determined by Matsuo et al., B.B.R.C. 43(6) 1334(1971) and Burgus et al., Proc. Natl. Acad. Sci. 69 278(1972) to be p-Glu-His-Trp-Ser-Tyr-Gly-Leu-Arg-Pro-Gly-NH$_2$. Shortly after the elucidation of the amino acid sequence of LH-RH it was found that changes of the amino acid residue in 2-position (His) markedly altered the activity of the decapeptide by diminishing or eliminating agonist activity with enhanced LH-RH antagonism. Rees et al., J. Med. Chem. 17(9) 1016(1974) found that [D-Trp$^2$]-LH-RH and [D-Phe$^2$]-Lh-RH antagonized LH release induced by LH-RH in vitro at a ratio of 1000:1 and 200:1, respectively, of their agonist (releasing) activity. Substitution of either L- or D-aliphatic amino acids in 2-position failed to afford products with meaningful antagonist activity. Beattie et al., J. Med. Chem. 18(12)1247(1975) report ten analogs of LH-RH substituted in 2-position with D-Phe, D-p-F-Phe or D-p-Cl-Phe and at 6-position with either a D-amino acid (D-Ala, D-Leu, D-Ser, D-Arg, D-(Ph)Gly, D-Lys) or 2-Me-Ala. The data demonstrated that no D-amino acid or non-asymmetric amino acid substitution in 6-position was more effective than D-Ala in potentiating antiovulatory activity. Rivier et al., Life Sciences 23 869(1978) report various polysubstituted LH-RH analogs such as [D-pGlu$^1$, D-Phe$^2$, D-Trp$^{3,6}$]-LH-RH which afforded an IDR$_{50}$ (inhibitory molar dose ratio-antagonist (LH-RH) of 3/1, in vitro. The effective dose for in vivo inhibition of ovulation was 20-25 mg when administered at noon of proestrus.

In studying LH-RH agonist analogues, Yabe et al. Chem. Pharm. Bull. 24(12) 3149(1976) noted that Nal(1)$^3$-LH-RH had 187.1 percent the potency of LH-RH as a leuteinizing hormone (LH) releasing agent.

DESCRIPTION OF THE INVENTION

In accordance with this invention there is provided a group of leuteinizing hormone releasing hormone (LH-RH) antagonists of the formula:

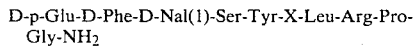

D-p-Glu-D-Phe-D-Nal(1)-Ser-Tyr-X-Leu-Arg-Pro-Gly-NH$_2$ in which

X is D-Nal(1), D-Trp, D-Phe, D-Tyr, D-Lys, D-Met, D-Ala or D-Pgl and pharmaceutically acceptable salts thereof. These compounds differ from LH-RH in the D-p-Glu$^1$, D-Phe$^2$, D-Nal(1)$^3$ amino acids and in the D-amino acids in 6-position of the decapeptide amide. In addition, the compounds of this invention inhibit ovulation in the mammal rather than induce it as does LH-RH and its agonistic analogues. Furthermore, the LH-RH antagonists of this invention exhibit approximately three times the potency observed with [D-Phe$^2$, D-Ala$^6$]LH-RH, which latter compound has been employed as the standard for measurement of LH-RH antagonism (See Beattie et al., supra).

The pharmaceutically acceptable salts of the decapeptides disclosed herein are derived from either organic or inorganic acids such as hydrochloric, hydrobromic, sulfuric, phosphoric, maleic, acetic, citric, benzoic, succinic, malic, ascorbic acids and the like. The interchange of one salt form with another is accomplished by methods well known to the medicinal chemist.

The novel decapeptides of this invention may be prepared by conventional solid phase synthesis employing a benzhydrylamine polystyrene resin such as is described by Rivaille et al., Helv. 54, 2772(1971). Such resins are commercially available for use in solid phase polypeptide synthesis. During the sequential coupling of amino acid residues to the initially bound glycine-benzhydrylamine resin support, those amino acids containing side chain functionality are blocked with protecting groups conventionally employed for that purpose. Examples of such protective groups may be found in U.S. Pat. No. 3,890,437, which patent is incorporated herein for its disclosure of applicable protecting groups.

The protected, resin bound decapeptide as well as the protected decapeptide amide after removal from the resin support are additional aspects of this invention depicted by the formula:

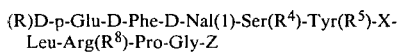

(R)D-p-Glu-D-Phe-D-Nal(1)-Ser(R$^4$)-Tyr(R$^5$)-X-Leu-Arg(R$^8$)-Pro-Gly-Z in which R is hydrogen or an alpha amino protecting group;
R$^4$ is a hydroxyl protecting group;
R$^5$ is a phenolic hydroxy protecting group;
R$^8$ is a nitrogen protecting group for the guanyl side chain of arginine and Z is —NH$_2$ or a benzhydryl amino resin support. When X is D-Tyr, an appropriate protecting group is selected from those representing R$^5$.

The preferred alpha amino protecting group is benzyloxycarbonyl(Boc) and the preferred protecting group for serine is benzyl(Bzl), for tyrosine is 2,6-dichlorobenzyl and for arginine is tosyl(Tos).

The following examples are illustrative of the preparation of the compounds of this invention.

EXAMPLE 1

N-Benzyloxycarbonyl-D-(5-oxoprolyl)-D-phenylalanyl-D-3-(1-naphthyl)-alanyl-O-benzyl-L-seryl-O-2,6-dichlorobenzyl-L-tyrosyl-D-3-(1-naphthyl)-alanyl-L-leucyl-N$^g$-tosyl-L-arginyl-L-prolylglycyl benzhydrylamine polystyrene Benzhydrylamine hydrochloride resin, 1% cross-linked (substitution range 0.4–0.6 mmoles/g resin, Bachem Inc.) (8 g.) was placed in a reaction vessel of a peptide synthesizer Beckman 990A and subjected to subsequent cycles of amino group deprotections and amino acid couplings as described in Program 1 and Program 2. The last program was performed in order to insure complete coupling of each amino acid. The following amino acids were incorporated onto the benzhydrylamine resin as described above: Boc-Gly-OH, Boc-Pro-OH, Boc-Arg(Tos)OH, Boc-Leu-OH, Boc-D-Nal-OH, Boc-Tyr-(2,6-Cl$_2$Bzl)-OH, Boc-Ser(Bzl)-OH, Boc-D-Nal-OH, Boc-D-Phe-OH, CBz-D-p-Glu-OH, to afford the title peptidoresin.

PROGRAM NO. 1

Peptide Synthesizer-Beckman 990

1. Wash with CH$_2$Cl$_2$ × 3.
2. Treat with TFA-CH$_2$Cl$_2$-EDT, 1:1:5% for 5 minutes.

3. Repeat (2) for 25 minutes.
4. Wash with CH$_2$Cl$_2$×4.
5. Treat with TEA 12% in DMF for 1 minute.
6. Repeat (5) for 5 minutes.
7. Wash with CH$_2$Cl$_2$×3.
8. Add 4 equivalents of Boc-protected amino acid and stir for 5 minutes. 9. Add 2 equivalents of 1M-DIC solution in DMF and stir for 25 minutes.
10. Add 2 equivalents of 1M-DIC solution in DMF and stir for 180 minutes.
11. Wash with CH$_2$Cl$_2$×3.
12. Wash with methanol×3.
13. Wash with CH$_2$Cl$_2$×3.

PROGRAM NO. 2

Peptide Synthesizer, Beckman 990

1. Wash with CH$_2$Cl$_2$×3.
2. Add 2 equivalents of Boc-protected amino acid and stir for 5 minutes.
3. Add 2 equivalents of 1M-DIC solution in DMF and stir for 180 minutes.
4. Wash with DMF×3.
5. Wash with CH$_2$Cl$_2$×3.
6. Wash with methanol×3.
7. Wash with CH$_2$Cl$_2$×3.

EXAMPLE 2

D-(5-Oxoprolyl)-D-phenylalanyl-D-3-(1-naphthyl)-alanyl-L-seryl-L-tyrosyl-D-3-(1-naphthyl)-alanyl-L-leucyl-L-arginyl-L-prolyl-glycine acetate salt The peptidoresin of the previous example (12 g.) was mixed with anisole (20 ml.) and treated with liquid HF (200 ml.) in an ice-bath and under vacuo for 60 minutes. The excess HF was evaporated under reduced pressure as fast as possible (ca. 60 minutes) and the residue was taken in 50% aqueous AcOH, filtered, and the filtrate was evaporated to a small volume in a rotary evaporator. The residue was chromatographed through a column (2.5×150 cm) of Sephadex G-25 and eluted with 50% aqueous AcOH. Fractions 68 to 115 were pooled and evaporated to dryness to afford 2.7 g. of the title compound. TLC silica gel precoated glass plates Analtech R$_f$ (n-BuOH-water-gl. AcOH, 4:1:1, v/v)0.50. Amino acid analysis: Ser (1) 1.05, Glu (1) 1.02, Pro (1) 1.03, Gly (1) 1.19, Leu (1) 0.96, Tyr (1) 0.96, Phe (1) 1, NH$_3$ (1) 1.32, Arg (1) 1.09, Nal N.D.

The anti-ovulatory activity of the decapeptides of this invention was established by the following procedure employing the product of Example 2 which demonstrates activity representative of the other compounds of the invention.

Mature Sprague-Dawley CD ® rats weighing 242±4.7 g., maintained on a 14:10 light:dark schedule, and which demonstrated at least two consecutive 4 day estrous cycles, were employed. The product of Example 2 was injected subcutaneously, in corn oil, as a single administration at 1200 hours on the day of proestrus (at least 2.5 hours prior to the commencement of the ovulatory LH surge). The rats were sacrificed on the morning of estrus (the day following proestrus) and the oviducts were inspected for the presence of ova under a dissecting microscope. The number of animals ovulating and the percent inhibition were as follows:

| 375 μg | 5/6 ovulated | 17% inhibition |
|---|---|---|
| 500 μg | 6/20 ovulated | 70% inhibition |
| 1000 μg | 1/14 ovulated | 93% inhibition |

Thus, the compounds of this invention are anti-ovulatory agents useful as contraceptive agents in the female mammal.

The contraceptive agents of this invention can be administered to the female mammal by intravenous, subcutaneous or intramuscular injection or orally or intra-nasally via a gel or or nebulized solution as well as intravaginally and intrarectally in appropriate vehicles. The dosage will vary with the form and route of administration and with the mammalian species being treated. Once established for a specific female, the dosage form and route can be routinely employed with consistent results. A typical dosage for parenteral administration contains from about 2 to about 5 milligrams/kilogram body weight.

What is claimed is:

1. A compound of the formula:

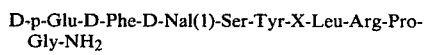

in which

X is D-Nal(1), D-Trp, D-Phe, D-Tyr, D-Lys, D-Met, D-Ala or D-Pgl and pharmaceutically acceptable salts thereof.

2. A compound of claim 1 which is D-(5-oxoprolyl)-D-phenylalanyl-D-3-(1-naphthyl)-alanyl-L-seryl-L-tyrosyl-D-3-(1-naphthyl)-alanyl-L-leucyl-L-arginyl-L-prolyl-glycine amide or a pharmaceutically acceptable salt thereof.

3. A compound of claim 1 which is D-(5-oxoprolyl)-D-phenylalanyl-D-3-(1-naphthyl)-alanyl-L-seryl-L-tyrosyl-D-tryptophyl-L-leucyl-L-arginyl-L-prolyl-glycine amide or a pharmaceutically acceptable salt thereof.

4. A compound of claim 1 which is D-(5-oxoprolyl)-D-phenylalanyl-D-3-(1-naphthyl)-alanyl-L-seryl-L-tyrosyl-D-phenylalanyl-L-leucyl-L-arginyl-L-prolyl-glycine amide or a pharmaceutically acceptable salt thereof.

5. A compound of claim 1 which is D-(5-oxoprolyl)-D-phenylalanyl-D-3-(1-naphthyl)alanyl-L-seryl-L-tyrosyl-D-tyrosyl-L-leucyl-L-arginyl-L-prolyl-glycine amide or a pharmaceutically acceptable salt thereof.

6. A compound of claim 1 which is D-(5-oxoprolyl)-D-phenylalanyl-D-3-(1-naphthyl)alanyl-L-seryl-L-tyrosyl-D-lysyl-L-leucyl-L-arginyl-L-prolyl-glycine amide or a pharmaceutically acceptable salt thereof.

7. A compound of claim 1 which is D-(5-oxoprolyl)-D-phenylalanyl-D-3-(1-naphthyl)alanyl-L-seryl-L-tyrosyl-D-methionyl-L-leucyl-L-arginyl-L-prolyl-glycine amide or a pharmaceutically acceptable salt thereof.

8. A compound of claim 1 which is D-(5-oxoprolyl)-D-phenylalanyl-D-3-(1-naphthyl)-alanyl-L-seryl-L-tyrosyl-D-alanyl-L-leucyl-L-arginyl-L-prolyl-glycine amide or a pharmaceutically acceptable salt thereof.

9. A compound of claim 1 which is D-(5-oxoprolyl-D-phenylalanyl-D-3-(1-naphthyl)alanyl-L-seryl-L-tyrosyl-D-phenyl-glycyl-L-leucyl-L-arginyl-L-prolyl-glycine amide or a pharmaceutically acceptable salt thereof.

10. A compound of the formula:

(R)D-p-Glu-D-Phe-D-Nal(1)-Ser($R^4$)-Tyr($R^5$)-X-Leu-Arg($R^8$)-Pro-Gly-Z in which
- R is hydrogen or an alpha amino protecting group;
- $R^4$ is a hydroxyl protecting group;
- $R^5$ is a phenolic hydroxy protecting group;
- $R^8$ is a nitrogen protecting group for the guanyl side chain of arginine;

and
- Z is a benzhydrylamine modified polystyrene resin support.

11. The compound of claim 10 which is N-benzyloxycarbonyl-D-(5-oxoprolyl)-D-phenylalanyl-D-3-(1-naphthyl)alanyl-O-benzyl-L-seryl-O-2,6-dichlorobenzyl-L-tyrosyl-D-3-(1-naphthyl)alanyl-L-leucyl-$N^g$-tosyl-L-arginyl-L-prolyl-glycyl-benzhydrylamine polystyrene.

* * * * *